US006693106B2

(12) United States Patent
Rahbar et al.

(10) Patent No.: US 6,693,106 B2
(45) Date of Patent: Feb. 17, 2004

(54) PENTOXIFYLLINE, PIOGLITAZONE AND METFORMIN ARE INHIBITORS OF FORMATION OF ADVANCED GLYCATION ENDPRODUCTS (AGE'S)

(75) Inventors: Samuel Rahbar, Encino, CA (US); Jerry L. Nadler, Charlottesville, VA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 10/096,579

(22) Filed: Mar. 14, 2002

(65) Prior Publication Data

US 2002/0128278 A1 Sep. 12, 2002

Related U.S. Application Data

(63) Continuation of application No. 09/559,913, filed on Apr. 28, 2000, now abandoned.
(60) Provisional application No. 60/131,675, filed on Apr. 29, 1999.

(51) Int. Cl.[7] ...................... A61K 31/522; A61K 31/425
(52) U.S. Cl. ............................ 514/263.34; 514/263.36; 514/263.38; 514/369
(58) Field of Search ........................ 514/263.34, 263.36, 514/263.38, 369

(56) References Cited

U.S. PATENT DOCUMENTS

| 4,921,997 | A |   | 5/1990  | Lalezari et al. |         |
|-----------|---|---|---------|-----------------|---------|
| 5,093,367 | A |   | 3/1992  | Lalezari et al. |         |
| 5,268,500 | A |   | 12/1993 | Lalezari et al. |         |
| 5,292,935 | A |   | 3/1994  | Lalezari et al. |         |
| 6,046,222 | A | * | 4/2000  | Antonucci et al.| 514/369 |
| 6,498,193 | B2| * | 12/2002 | Beisswenger et al.| 514/635 |

OTHER PUBLICATIONS

Ferrari et al, "Effects of long term treatment (4 years) with pentoxifylline . . . ", Pharmatherapeutics, vol. 5, No. 1 (1987).*
Al–Abed, Y. et al. "Inhibition of advanced glycation endproduct formation by acetaldehyde: Role in the cardioprotective effect of ethanol", *Proc. Natl. Acad. Sci. USA*, Mar. 1999; 96:2385–2390.
Asif, M. et al. "An advanced glycation endproduct cross–link breaker can reverse age–related increases in myocardial stiffness", *PNAS*, Mar. 14, 2000; 97(6):2809–2813.
Beisswenger, P.J. et al. "Metformin Reduces Systemic Methylglyoxal Levels in Type 2 Diabetes", *Diabetes*, Jan. 1999; 48:198–202.
Boel, E. et al. "Diabetic Late Complications: Will Aldose Reductase Inhibitors or Inhibitors of Advanced Glycosylation Endproduct Formation Hold Promise?", *J. Diabetes and Its Complications*, 1995; 9:104–129.

Booth, A.A. et al. "Thiamine Pyrophosphate and Pyridoxamine Inhibit the Formation of Antigenic Advanced Glycation End–Products: Comparison with Aminoguanidine", *Biochem. Biophys. Res. Commun.*, 1996; 220:113–119.

Booth, A.A. et al. "In Vitro Kinetic Studies of Formation of Antigenic Advanced Glycation End Products (AGEs)", *Journal of Biological Chemistry*, Feb. 28, 1997; 272(9):5430–5437.

Cameron, N.E. et al. "Effects of aminoguanidine on peripheral nerve function and polyol pathway metabolites in streptozotocin–diabetic rats", *Diabetologia*; 1992; 35:946–950.

Corbett, J.A. et al. "Aminoguanidine, a Novel Inhibitor of Nitric Oxide Formation, Prevents Diabetic Vascular Dysfunction", *Diabetes*, Apr. 1992; 41:552–556.

Durany, N. et al. "Investigations on oxidative stress and therapeutical implications in dementia", *Eur. Arch. Psychiatry Clin. Neurosci.*, 1999; 249:Suppl. 3 III/68–III/73.

Jakus, V. et al. "Inhibition of Nonenzymatic Protein Glycation and Lipdi Peroxidation by Drugs with Antioxidant Activity", *Life Sciences*, 1999; 65(18–19):1991–1993.

Jyothirmayi, G.N. et al. "Effects of Metformin on Collagen Glycation and Diastolic Dysfunction in Diabetic Myocardium", *J. Cardiovasc. Pharmacol. Therapeut.*, 1998; 3(4):319–326.

Khalifah, R.G. "Amadorins: Novel Post–Amadori Inhibitors of Advanced Glycation Reactions", *Biochem. Biophys. Res. Commun.*, 1999; 257:251–258.

(List continued on next page.)

Primary Examiner—Frederick Krass
(74) Attorney, Agent, or Firm—Rothwell, Figg, Ernst & Manbeck

(57) ABSTRACT

Pentoxifylline, pioglitazone and metformin have been found to inhibit the nonenzymatic glycation of proteins which often results in formation of advanced glycation endproducts and crosslinks. The nonenzymatic glycation and crosslinking of proteins is a part of the aging process with the glycation endproducts and crosslinking of long-lived proteins increasing with age. This process is increased at elevated concentrations of reducing sugars in the blood and in the intracellular environment such as occurs with diabetes. The structural and functional integrity of the affected molecules become perturbed by these modifications and can result in severe consequences. The compounds of the present invention can be used to inhibit this process of nonenzymatic glycation and therefore to inhibit some of the ill effects caused by diabetes or by aging. The compounds are also useful for preventing premature aging, rheumatoid arthritis, Alzheimer's disease, uremia, neurotoxicity, atherosclerosis and spoilage of proteins in food and can prevent discoloration of teeth.

2 Claims, 5 Drawing Sheets

OTHER PUBLICATIONS

Kochakian, M. et al. "Chronic Dosing with Aminoguanidine and Novel Advanced Glycosylation End Product–Formation Inhibitors Ameliorates Cross–Linking of Tail Tendon Collagen and STZ–Induced Diabetic Rats", *Diabetes*, Dec. 1996; 45:1694–1700.

Lalezari, I. et al. "Synthesis and Investigation of Effects of 2–[4–[[(Arylamino)carbonyl]amino]phenoxy]–2–methyl-propionic Acids on the Affinity of Hemoglobin for Oxygen: Structure–Activity Relationships", *J. Med. Chem.*, 1989; 32:2352–2357.

Lalezari, I. et al. "LR16, a compound with potent effects on the oxygen affinity of hemoglobin, on blood cholesterol, and on low density lipoprotein", *Proc. Natl. Acad. Sci. USA*, Aug. 1988; 85:6117–6121.

Malik, N.S. and Meek, K.M. "The Inhibition of Sugar–Induced Structural Alterations in Collagen by Aspirin and Other Compounds", *Biochem. Biophys. Res. Commun.*, 1994; 199(2):683–686.

Marques, C. et al. "Bendazac decreases in vitro glycation of human lens crystallins. Decrease of in vitro protein glycation by bendazac", *Documenta Ophthalmologica*, 1995; 90:395–404.

Menzel, E.J. et al. "Comparison of the effect of different inhibitors on the non–enzymatic glycation of rat tail tendons and bovine serum albumin", *Ann. Clin. Biochem.*, 1996; 33:241–248.

Miwa, I. et al. "Inhibition of Advanced Protein Glycation by 8–Quinolinecarboxylic Hydrazide", *Pharmacology*, 1996; 52:314–320.

Morimitsu, Y. et al. "Protein Glycation Inhibitors from Thyme (*Thymus vulgaris*)", *Biosci. Biotech. Biochem.*, 1995; 59(11):2018–2021.

Münch, G. et al. "Influence of advanced glycation end–products and AGE–inhibitors on nucleation–dependent polymerization of β–amyloid peptide", *Biochimica et Biophysica Acta*, 1997; 1360:17–29.

Münch, G. et al. "Advanced glycation endproducts in ageing and Alzheimer's disease", *Brain Research Reviews*, 1997; 23:134–143.

Nakamura, S. et al. "Progression of Nephropathy in Spontaneous Diabetic Rats is Prevented by OPB–9195, a Novel Inhibitor of Advanced Glycation", *Diabetes*, May 1997; 46:895–899.

Rahbar, S. and Nadler, J.L. "A new rapid method to detect inhibition of Amadori product generated by δ–gluconolactone", *Clinica Chimica Acta*, 1999; 287:123–130.

Rahbar, S. et al. "Novel Inhibitors of Advanced Glycation Endproducts", *Biochem. Biophys. Res. Commun.*, 1999; 262:651–656.

Ruggiero–Lopez, D. et al. "Reaction of Metformin with Dicarbonyl Compounds. Possible Implication in the Inhibition of Advanced Glycation End Product Formation", *Biochem. Pharmacology*, 1999; 58:1765–1773.

Ryan, M.E. et al. "Tetracyclines Inhibit Protein Glycation in Experimental Diabetes", *Adv. Dent. Res.*, Nov. 1998; 12:152–158.

Sensi, M. et al. "D–Lysine reduces the non–enzymatic glycation of proteins in experimental diabetes mellitus in rats", *Diabetologia*, 1993; 36:797–801.

Soulis, T. et al. "Relative contributions of advanced glycation and nitric oxide synthase inhibition to aminoguanidine–mediated renoprotection in diabetic rats", *Diabetologia*, 1997; 40:1141–1151.

Soulis, T. et al. "A novel inhibitor of advanced glycation end–product formation inhibits mesenteric vascular hypertrophy in experimental diabetes", *Diabetologia* 1999; 42:472–479.

Swamy–Mruthinti, S. et al. "Acetyl–L–Carnitine Decreases Glycation of Lens Proteins: in vitro Studies", *Exp. Eye Res.*, 1999; 69:109–115.

Taguchi, T. et al. "Inhibition of advanced protein glycation by a Schiff base between aminoguanidine and pyridoxal", *European Journal of Pharmacology*, 1999; 378:283–289.

Tanaka, Y. et al. "Effect of metformin on advanced glycation endproduct formation and peripheral nerve function in streptozotocin–induced diabetic rats", *European Journal of Pharmacology*, 1999; 376:17–22.

Tilton, R.G. et al. "Prevention of Diabetic Vascular Dysfunction by Guanidines. Inhibition of Nitric Oxide Synthase Versus Advanced Glycation End–Product Formation", *Diabetes*, Feb. 1993; 42:221–232.

Tsuchida, K. et al. "Suppression of transforming growth factor beta and vascular endothelial growth factor in diabetic nephropathy in rats by a novel advanced glycation end product inhibitor, OPB–9195", *Diabetologia*, 1999; 42:579–588.

Ulrich, P. and Zhang, X. "Pharmacological reversal of advanced glycation end–product–mediated protein crosslinking", *Diabetologia*, 1997; 40:S157–S159.

van Boekel, M. et al. "Glycation of human serum albumin: inhibition by Diclofenac", *Biochimica et Biophysica Acta*, 1992; 1120:201–204.

Vasan, S. et al. "An agent cleaving glucose–derived protein crosslinks in vitro and in vivo", *Nature*, Jul. 18, 1996; 382:275–278.

Wolffenbuttel, B. et al. "Breakers of advanced glycation end products restore large artery properties in experimental diabetes", *Proc. Natl. Acad. Sci. USA*, Apr. 1998; 95:4630–4634.

\* cited by examiner

PENTOXIFYLLINE, PIOGLITAZONE AND METFORMIN ARE INHIBITORS OF FORMATION OF ADVANCED GLYCATION ENDPRODUCTS (AGE'S)

CROSS-REFERENCE TO RELATED APPLICATIONS

This application is a continuation of Ser. No. 09/559,913, filed Apr. 28, 2000, now abandoned, which claims priority from Serial No. 60/131,675, filed Apr. 29, 1999, which is incorporated herein in its entirety.

BACKGROUND OF THE INVENTION

The present invention relates generally to the modification and aging of proteins through reaction with glucose and other reducing sugars, such as fructose or ribose and more particularly to the inhibition of nonenzymatic glycation of proteins which often results in formation of advanced glycation endproducts and crosslinks.

An elevated concentration of reducing sugars in the blood and in the intracellular environment results in the nonenzymatic formation of glycation and dehydration condensation complexes known as advanced glycation end-products (AGE's). These complex products form on free amino groups on proteins, on lipids and on DNA (Bucala and Cerami, 1992; Bucala et al., 1993; Bucala et al., 1984). This phenomenon is called "browning" or "Maillard" reaction and was discovered early in this century by the food industry (Maillard, 1916). The significance of a similar process in biology became evident only after the discovery of the glycosylated hemoglobins and their increased presence in diabetic patients (Rahbar, 1968; Rahbar et al., 1969). In human diabetic patients and in animal models of diabetes, these nonenzymatic reactions are accelerated and cause increased AGE formation and increased glycation of long-lived proteins such as collagen, fibronectin, tubulin, lens crystallin, myelin, laminin and actin, in addition to hemoglobin and albumin, and also of LDL associated lipids and apoprotein. Moreover, brown pigments with spectral and fluorescent properties similar to those of late-stage Maillard products have also been found in vivo in association with several long-lived proteins such as lens crystallin proteins and collagen from aged individuals. An age-related linear increase in pigments was observed in human dura collagen between the ages of 20 to 90 years. AGE modified proteins increase slowly with aging and are thought to contripbute to normal tissue remodeling. Their level increases markedly in diabetic patients as a result of sustained high blood sugar levels and lead to tissue damage through a variety of mechanisms including alteration of tissue protein structure and function, stimulation of cellular responses through AGE specific receptors or the generation of reactive oxygen species (ROS) (for a recent review see Boel et al., 1995). The structural and functional integrity of the affected molecules, which often have major roles in cellular functions, become perturbed by these modifications, with severe consequences on affected organs such as kidney, eye, nerve, and micro-vascular functions (Silbiger et al., 1993; Brownlee et al., 1985).

Structural changes on macromolecules by AGE's are known to accumulate under normal circumstances with increasing age. This accumulation is severely accelerated by diabetes and is strongly associated with hyperglycemia. For example, formation of AGE on protein in the subendothelial basement membrane causes extensive cross-link formation which leads to severe structural and functional changes in protein/protein and protein/cell interaction in the vascular wall (Haitoglou et al., 1992; Airaksinen et al., 1993).

Enhanced formation and accumulation of advanced glycation end products (AGE's) have been proposed to play a major role in the pathogenesis of diabetic complications and in aging, leading to progressive and irreversible intermolecular protein crosslinkings (Monnier et al., 1986). This process is accelerated by diabetes and has been postulated to contribute to the development of a range of diabetic complications including nephropathy (Nicholls and Mandel, 1989), retinopathy (Hammes et al., 1991) and neuropathy (Cameron et al., 1992). Particularly, tissue damage to the kidney by AGE's leads to progressive decline in renal function and end-stage renal disease (ESRD) (Makita et al., 1994), and accumulation of low-molecular-weight (LMW) AGE peptides (glycotoxins) (Koschinsky et al., 1997) in the serum of patients with ESRD (Makita et al., 1991). These low molecular weight (LMW)-AGE's can readily form new crosslinks with plasma or tissue components, e.g., low density lipoprotein (LDL) (Bucala et al., 1994) or collagen (Miyata et al., 1993) and accelerate the progression of tissue damage and morbidity in diabetics.

The Diabetic Control and Complications Trial (DCCT), has identified hyperglycemia as the main risk-factor for the development of diabetic complications (The Diabetes Control and Complications Trial Research Group, 1993). Although there is no consensus regarding the pathogenic link between hyperglycemia and diabetic complications, formation of advanced glycation endproducts (AGE's) has been implicated as a major pathogenic process in the long-term complications of diabetes, namely nephropathy, neuropathy and retinopathy.

Particularly, tissue damage to the kidney by AGE's leads to progressive decline in renal function and end-stage renal failure (ESRD) (Makita et al., 1994), and accumulation of low-molecular-weight (LMW) AGE peptides (glycotoxins) (Koschinsky et al., 1997) in the serum of patients with ESRD (Makita et al., 1991). These low molecular weight (LMW)-AGE's can readily form new cross-links with plasma or tissue components, e.g., low density lipoprotein (LDL) (Bucala et al., 1994) or collagen (Baily et al., 1998) and accelerate the progression of tissue damage and morbidity in diabetes.

Although the mechanism of non-enzymatic glycation is not completely understood and the precise structures of major AGE components remain to be established, α-dicarbonyl compounds have been identified as major intermediates in the glycation pathways and cross-linking of proteins by glucose (Baynes and Thorpe, 1999). Hyperglycemia is associated with the formation of dicarbonyl compounds, particularly methylglyoxal (MGO), glyoxal (GO), 3-deoxyglucosone (3-DG), glycoaldehyde and dehydroascorbate (Onorato et al., 1998). In patients with both insulin-dependent and non-insulin dependent diabetes, the concentration of MGO was found to be increased 2–6-fold (McLellan et al., 1994). The major source of MGO is thought to be the non-enzymatic dephosphorylation of the triosedihydroxyacetone phosphate and glyceraldehyde-3-phosphate. In addition, glucose auto-oxidation and degradation of Amadori products and enzymatic catabolism of acetone through the acetol pathway (Phillips and Thornalley, 1993) are alternative sources of MGO formation. The glyoxylase system (I and II) and aldose reductase catalyze the detoxification of MGO to D-lactate. MGO binds to and irreversibly modifies arginine and lysine residues in proteins. MGO modified proteins have been shown to be ligands for the AGE receptor (Beisswenger et al., 1998), indicating that MGO modified proteins are analogous (Beisswenger et al., 1998) to those found in AGE's. Most recently, the effects of MGO on LDL has been characterized in vivo and in vitro (Westwood et al., 1997).

Lipid peroxidation of polyunsaturated fatty acids (PUFA), such as arachidonate, also yield carbonyl compounds; some are identical to those formed from carbohydrates (Schalkwijk et al., 1998), such as MGO and GO, and others are characteristic of lipid, such as malondialdehyde (MDA) and 4-hydroxynonenal (HNE) (Bucala et al., 1993). The latter carbonyl compounds produce lipoxidation products, such as MDA-lysine, lysine-MDA-lysine, HNE-protein adducts (HNE Lys, His, Cys) (Al-Abed et al., 1996). AGE compounds characterized in vitro and in vivo are either the result of glycation alone or glycation-oxidation modification called glycoxidation products. Glycoxidation products that have been detected in tissue proteins are $N^\epsilon$-carboxymethyl-lysine (CML), $N^\epsilon$-carboxyethyl-lysine (CEL), $N^\epsilon$-carboxymethyl-ethanolamine (CME) (Requena et al., 1997), pentosidine, glyoxal-lysine-dimer (GOLD) and methylglyoxal-lysine-dimer (MOLD). These products may be derived from either glycoxidation or lipoxidation reactions. Other AGE's detected in tissue proteins are pyrraline, crossline imidazolium salts formed by the reaction of MOLD or GOLD and imidazolones formed by the reaction of MGO or 3-DG with arginine. Most of the above AGE's are involved in cross-linking of proteins. Furthermore, MGO has been found not only as the most reactive dicarbonyl AGE-intermediate in cross-linking of proteins, a recent report has found MGO to generate reactive oxygen species (ROS) (free radicals) in the course of glycation reactions (Yim et al., 1995). Indeed, three types of free radical species were produced and their structures were determined by EPR spectroscopy. The superoxide radical anion was produced only in the presence of oxygen in these reactions, more evidence that ROS are generated during glycation reaction and AGE-formation.

These findings and other reports provided evidence that indeed oxidative stress and AGE-formation are undividedly intertwined. Oxidative stress is apparent in pathology associated with aging and common end points of chronic diseases, such as atherosclerosis, diabetes, rheumatoid arthritis and uremia (Baynes and Thorpe, 1999). What is not clear is whether oxidative stress has a primary role in the pathogenesis of diabetic complications or whether it is a secondary indicator of end-stage tissue damage in diabetes (Baynes and Thorpe, 1999). The increase in glycoxidation and lipoxidation products in plasma and tissue proteins suggests that oxidative stress is in fact increased in diabetes (Baynes, 1996). The issue is whether oxidation stress occurs at early stage in diabetes, preceding the appearance of complications, or whether it is merely a common consequence of the tissue damage, reflecting the presence of complications. Several lines of evidence indicated that one of the critical pathogenic consequences of hyperglycemia in diabetes is a deficit in detoxification of reactive carbonyl (dicarbonyl) compounds. The increase in reactive carbonyls derived from both oxidative and nonoxidative reactions (defined as carbonyl stress) leads to increased chemical modification of proteins, and then, at a late stage, to oxidant stress and tissue damage. Thus, intervention should begin at the level of carbonyl stress, long before the appearance of overt oxidative stress and damage (Baynes and Thorpe, 1999).

Direct evidence indicating the contribution of AGE's in the progression of diabetic nephropathy has recently been reported (Vlassara et al., 1994). Indeed, the infusion of pre-formed AGE's into healthy rats induces glomerular hypertrophy and mesangial sclerosis, gene expression of matrix proteins and production of growth factors (Brownlee et al., 1991; Vlassara et al., 1995). Further studies have revealed that aminoguanidine (AG), an inhibitor of AGE formation, ameliorates tissue impairment of glomeruli and reduces albuminuria in induced diabetic rats (Soulis-Liparota et al., 1991; Itakura et al., 1991). In humans, decreased levels of hemoglobin (Hb)-AGE (Makita et al., 1992) concomitant with amelioration of kidney function as the result of aminoguanidine therapy in diabetic patients, provided more evidence for the importance of AGE's in the pathogenesis of diabetic complications (Bucala and Vlassara, 1997).

The global prevalence of diabetes mellitus, in particular in the United States, afflicting millions of individuals with significant increases of morbidity and mortality, together with the great financial burden for the treatment of diabetic complications in this country, are major incentives to search for and develop drugs with a potential of preventing or treating complications of the disease. So far the mechanisms of hyperglycemia-induced tissue damage in diabetes are not well understood. However, four pathogenic mechanisms have been proposed, including increased polyol pathway activity, activation of specific protein kinase C (PKC) isoforms, formation and accumulation of advanced glycation endproducts, and increased generation of reactive oxygen species (ROS) (Kennedy and Lyons, 1997). Most recent immunohistochemical studies on different tissues from kidneys obtained from ESRD patients (Horie et al., 1997) and diabetic rat lenses (Matsumoto et al., 1997), by using specific antibodies against carboxymethyllysine (CML), pentosidine, the two known glycoxidation products and pyrraline, have localized these AGE components in different lesions of the kidneys and the rat lens, and have provided more evidence in favor of protein-AGE formation in close association with generation of ROS to be major factors in causing permanent and irreversible modification of tissue proteins. Therefore, inhibitors of AGE formation and antioxidants hold promise as effective means of prevention and treatment of diabetic complications.

In addition to aging and diabetes, the formation of AGEs has been linked with several other pathological conditions. IgM anti-IgG-AGE appears to be associated with clinical measurements of rheumatoid arthritis activity (Lucey et al., 2000). A correlation between AGEs and rheumatoid arthritis was also made in North American Indians (Newkirk et al., 1998). AGEs are present in brain plaques in Alzheimer's disease and the presence of AGEs may help promote the development of Alzheimer's disease (Durany et al., 1999; Munch et al., 1998; Munch et al., 1997). Uremic patients have elevated levels of serum AGEs compared to age-matched controls (Odani et al., 1999; Dawnay and Millar, 1998). AGEs have also been correlated with neurotoxicity (Kikuchi et al., 1999). AGE proteins have been associated with atherosclerosis in mice (Sano et al., 1999) and with atherosclerosis in persons undergoing hemodialysis (Takayama et al., 1998). A study in which aminoguanidine was fed to rabbits showed that increasing amounts of aminoguanidine led to reduced plaque formation in the aorta thus suggesting that advanced glycation may participate in atherogenesis and raising the possibility that inhibitors of advanced glycation may retard the process (Panagiotopoulos et al., 1998). Significant deposition of N(epsilon)-carboxymethyl lysine (CML), an advanced glycation endproduct, is seen in astrocytic hyaline inclusions in persons with familial amyotrophic lateral sclerosis but is not seen in normal control samples (Kato et al., 1999; Shibata et al., 1999). Cigarette smoking has also been linked to increased accumulation of AGEs on plasma low density lipoprotein, structural proteins in the vascular wall, and the lens proteins of the eye, with some of these effects possibly leading to pathogenesis of atherosclerosis and other diseases associated with tobacco usage (Nicholl and Bucala, 1998). Finally, a study in which aminoguanidine was fed to rats showed that the treatment protected against progressive cardiovascular and renal decline (Li et al., 1996).

The mechanism of the inhibitory effects of aminoguanidine has been investigated and it has been demonstrated that AG acts as a general-carbonyl scavenger, trapping both oxidative and nonoxidative AGE precursors as well as intermediates in lipid peroxidation reactions (Chen and Cerami, 1993). In vitro and in vivo studies indicated the AG reacts with MGO to produce substituted triazines (Chen and Cerami, 1993). Most recently, metformin, one of the drugs used for many years in the treatment of type 2 diabetes, was demonstrated to inactivate and reduce MGO levels both in vivo and in vitro (Beisswenger et al., 1999), indicating the inhibitory function of metformin in AGE-formation. Despite the limitations of our current knowledge, there is leading evidence that trapping of reactive carbonyl compounds, the chemical intermediates between hyperglycemia/hyperlipidemia and diabetic complications, may be a valuable strategy for inhibiting or delaying diabetic complications (Baynes and Thorpe, 1999). Considering the diversities of these carbonyl intermediates, different drugs with diverse structures could be discovered as inhibitors of carbonyl compounds.

Several other potential drug candidates as AGE inhibitors have been reported recently. These studies evaluated the agent's ability to inhibit AGE formation and AGE-protein crosslinking compared to that of aminoguanidine (AG) through in vitro and in vivo evaluations (Nakamura et al., 1997; Kochakian et al., 1996). A recent breakthrough in this field is the discovery of a compound, N-phenacylthiazolium bromide (PTB), which selectively cleaves AGE-derived protein crosslinks in vitro and in vivo (Vasan et al., 1996; Ulrich and Zhang, 1997). The pharmacological ability to break irreversible AGE-mediated protein crosslinking offers potential therapeutic use.

It is well documented that early pharmaceutical intervention against the long-term consequences of hyperglycemia-induced crosslinking prevent the development of severe late complications of diabetes. The development of nontoxic and highly effective drugs that completely stop glucose-mediated crosslinking in the tissues and body fluids is a highly desirable goal. The prototype of the pharmaceutical compounds investigated both in vitro and in vivo to intervene with the formation of AGE's on proteins is aminoguanidine (AG), a small hydrazine-like compound (Brownlee et al., 1986). However, a number of other compounds were found to have such an inhibitory effect on AGE formation. Examples are D-lysine (Sensi et al., 1993), desferrioxamine (Takagi et al., 1995), D-penicillamine (McPherson et al., 1988), thiamine pyrophosphate and pyridoxamine (Booth et al., 1997) which have no structural similarities to aminoguanidine.

Clinical trials of AG as the first drug candidate intended to inhibit AGE formation are in progress (Corbett et al., 1992). A number of hydrazine-like and non-hydrazine compounds have been investigated. So far AG has been found to be the most useful with fewer side effects than other tested compounds of the prior art. However, AG is a well known selective inhibitor of nitric oxide (NO) and can also have antioxidant effects (Tilton et al., 1993).

A number of other potential drug candidates to be used as AGE inhibitors have been discovered recently and evaluated both in vitro and in vivo (Nakamura et al., 1997; Soulis et al., 1997). While the success in studies with aminoguanidine and similar compounds is promising, the need to develop additional inhibitors of AGE's continues to exist in order to broaden the availability and the scope of this activity and therapeutic utility.

SUMMARY OF THE INVENTION

Pentoxifylline, pioglitazone and metformin have been found to inhibit the nonenzymatic glycation of proteins which often results in formation of advanced glycation endproducts and crosslinks. The nonenzymatic glycation and crosslinking of proteins is a part of the aging process with the glycation endproducts and crosslinking of long-lived proteins increasing with age. This process is increased at elevated concentrations of reducing sugars in the blood and in the intracellular environment such as occurs with diabetes. The structural and functional integrity of the affected molecules become perturbed by these modifications and can result in severe consequences. The compounds of the present invention can be used to inhibit this process of nonenzymatic glycation and crosslinking and therefore to inhibit some of the ill effects caused by diabetes or by aging. The compounds are also useful for preventing premature aging, rheumatoid arthritis, Alzheimer's disease, uremia, neurotoxicity, atherosclerosis and spoilage of proteins in food and can prevent discoloration of teeth.

DETAILED DESCRIPTION OF THE INVENTION

Figure 1:
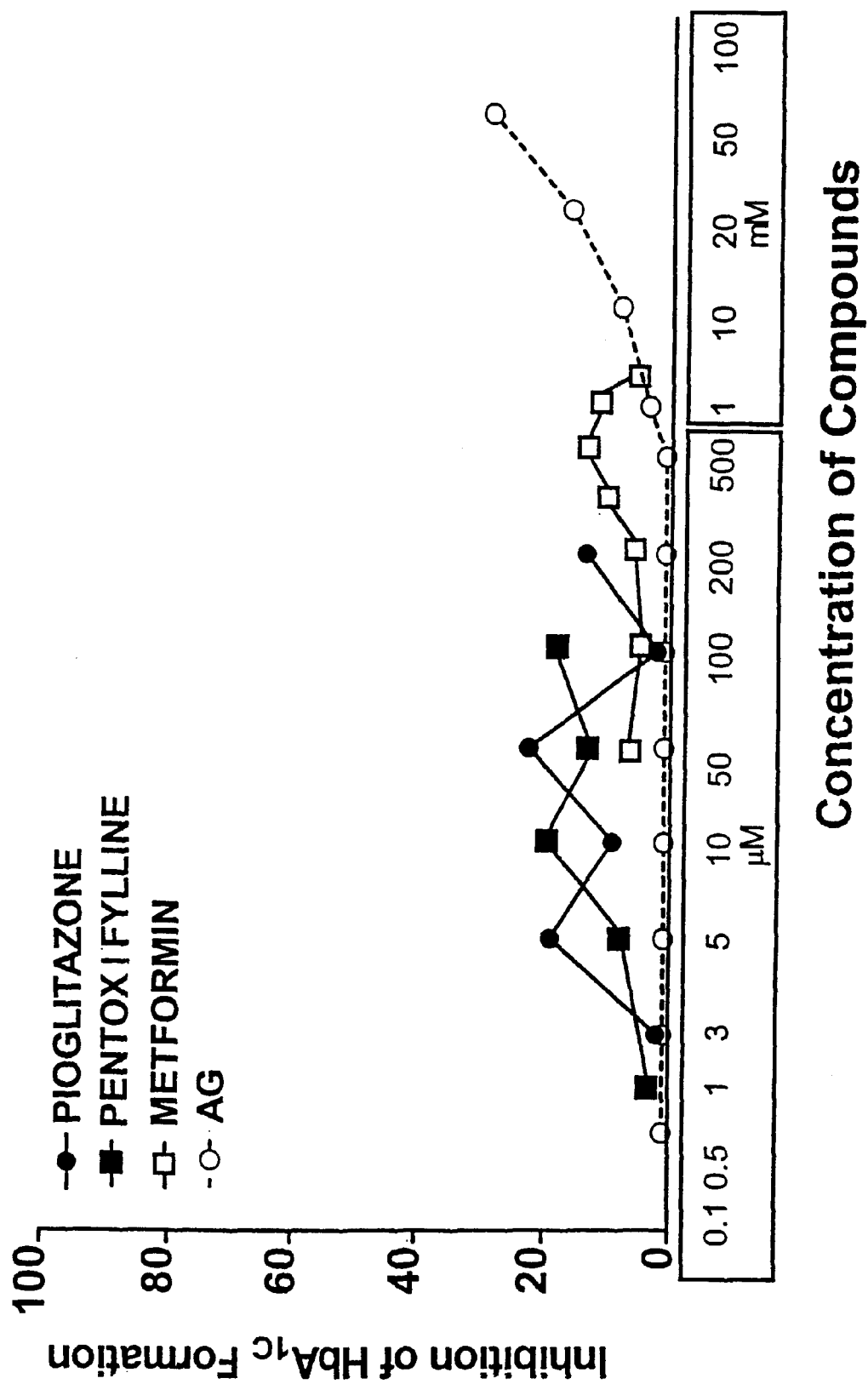
FIG. 1 demonstrates composite dose-response curves of metformin, pioglitazone and pentoxifylline and of aminoguanidine (AG), used as a positive control. Various concentrations of an inhibitor compound were incubated with whole blood and δ-Glu for 16 hours at 37° C. followed by determinations of $HbA_{1C}$ in the test and the control tubes. The percent inhibition of $HbA_{1C}$ by various concentrations of an inhibitor compounds were plotted.

In the course of screening different classes of organic compounds for investigation of their possible inhibitory effects on advanced glycation endproducts (AGE's), we found that pentoxifylline, pioglitazone and metformin each have inhibitory effects and these compounds are potent inhibitors of AGE-formation at concentrations much lower than an equally inhibiting concentration of aminoguanidine.

The compounds and their useful compositions utilized in the present invention contain agents capable of reacting with the highly active carbonyl intermediate of an early glycation product thereby preventing those early products from later forming the advanced glycation endproducts which lead to protein cross-linking and to protein aging.

Other utilities envisioned for the present invention are prevention of premature aging and of spoilage of the proteins in foodstuffs. The present agents are also useful in the area of oral hygiene as they prevent discoloration of teeth.

Compounds

The compounds of the present invention are pentoxifylline, pioglitazone and metformin. Pentoxifylline is 3,7-dihydro-3,7-dimethyl-1-(5-oxohexyl)-1H-purine-2,6-dione and is also known as Trental. Previous studies have shown this compound to be non-toxic and it may be administered orally, parenterally or rectally. Pioglitazone is 5-[[4-[2-(5-ethyl-2-pyridinyl)-ethoxy]phenyl]methyl]-2,4-thiazolidinedione. Previous studies have shown this compound to be non-toxic and it may be administered orally. Pioglitazone is among other thiazolidinedione compounds such as Troglitazone and Rosiglitazone which have recently been in therapeutic uses for the treatment of type 2 diabetes mellitus, lowering the blood sugar as well as hemoglobin A1C. Metformin is 1,1-dimethylbiguanide and is also known as glucophage. Previous studies have shown that this compound also is non-toxic and may be administered orally. Metformin has been in therapeutic use for the treatment of type 2 diabetes mellitus, lowering blood sugar. The present invention relates to the uses of metformin for preventing the complications of diabetes and aging independent of its blood sugar lowering.

The above three compounds are capable of inhibiting the formation of advanced glycation end products on target proteins and the resulting protein crosslinking. The rationale of the present invention is to use agents which block the post-glycation step, i.e., the formation of fluorescent chromophores, the presence of which chromophore is associated with and leads to adverse sequelae of diabetes and aging. An ideal agent would prevent the formation of the chromophore and its associated cross-links of proteins and trapping of proteins on the other proteins, such as occurs in arteries and in the kidneys. The compounds of the invention may be administered to mammals including humans to prevent or reduce protein glycation and cross-linking (protein aging). The compounds may be administered orally at variable dosage depending on the activity of each agent in a single or individual amount. In addition the compounds may be administered parenterally or rectally. The compounds of the invention, the rationale behind the different assay methods of the present invention, and their use are illustrated by the following Examples.

EXAMPLE 1

Hemoglobin-δ-Gluconolactone (δ-Glu) Assay

Evaluation of early glycation products (Amadori) formation on hemoglobin ($HbA_{1C}$) is performed by incubating red blood cells with an oxidized form of glucose in the presence and the absence of the inhibitor compound followed by determination of ($HbA_{1C}$) in the test versus the control (Rahbar and Nadler, 1999). This test is based on a recent report by Lindsay et al. (1997). δ-Glu, an oxidized analogue of glucose, can react rapidly with hemoglobin within the red cells and significantly increases the $HbA_{1C}$ levels within hours after incubation. By contrast, glucose requires weeks for an equivalent reaction to occur. We have used this finding to devise an assay method to measure early stage glycation of hemoglobin (Amadori product) and an assay to evaluate the ability of an inhibitor to inhibit $HbA_{1C}$ formation. Briefly, fresh blood was drawn in potassium-EDTA and prepared for incubation within 30 minutes of collection by mixing 200 μL of blood with 40 μL of either phosphate buffered-saline (PBS), pH 7.4, alone, PBS containing 50 millimoles/L δ-Glu (Sigma), or PBS containing 50 millimoles/L δ-Glu plus 1 millimole/L inhibitor. After incubation for 16 hours at 37° C., the percentage of glycated hemoglobin present was determined. The percentage of glycated Hb ($HbA_{1C}$) was determined using a dedicated ion-exchange HPLC system (BIORAD DIAMAT). Blood samples were analyzed in triplicate. The % inhibition of $HbA_{1C}$ formation by the compound was calculated according to the following formula:

$$((B-C)/(B-A)) \times 100$$

where A is $HbA_{1C}$ concentration in the baseline control tube not treated with δ-Glu, B is the $HbA_{1C}$ concentration in blood incubated with δ-Glu, C is the $HbA_{1C}$ content of the test tube treated both with δ-Glu and the inhibitor compound.

The amount of ($HbA_{1C}$) formation using δ-Glu treated whole blood from normal volunteers using a range of concentrations of the compounds is shown in FIG. 1. The δ-Glu assay is a specific method for investigation of inhibitors of early stage of glycation. The results of this assay show that pioglitazone, pentoxifylline and metformin have moderate inhibitory effects on the early stage of glycation.

The above experiment suggests that this type of drug therapy has benefits in reducing the pathology associated with the formation of early glycation products, a preliminary step in the advanced glycation end product formation.

EXAMPLE 2

BSA-Glucose Assay

This test is used to evaluate the ability of the inhibitors to inhibit glucose-mediated development of fluorescence of BSA (Ikeda et al., 1996). BSA (fraction V) from Sigma 50 mg/mL and 800 mM glucose (144 mg/mL) in 1.5 M phosphate buffer pH 7.4 containing $NaN_3$ 0.2 g/L was incubated under aseptic conditions at 37° C. for 7 days in the presence or absence of various concentrations of the compounds. After 7 days of incubation each sample was examined for the development of specific fluorescence (excitation, 370 nm; emission, 440 nm). The % inhibition of AGE formation in the test sample versus control was calculated for each inhibitor compound. Aminoguanidine was used as a positive control.

Figure 2:
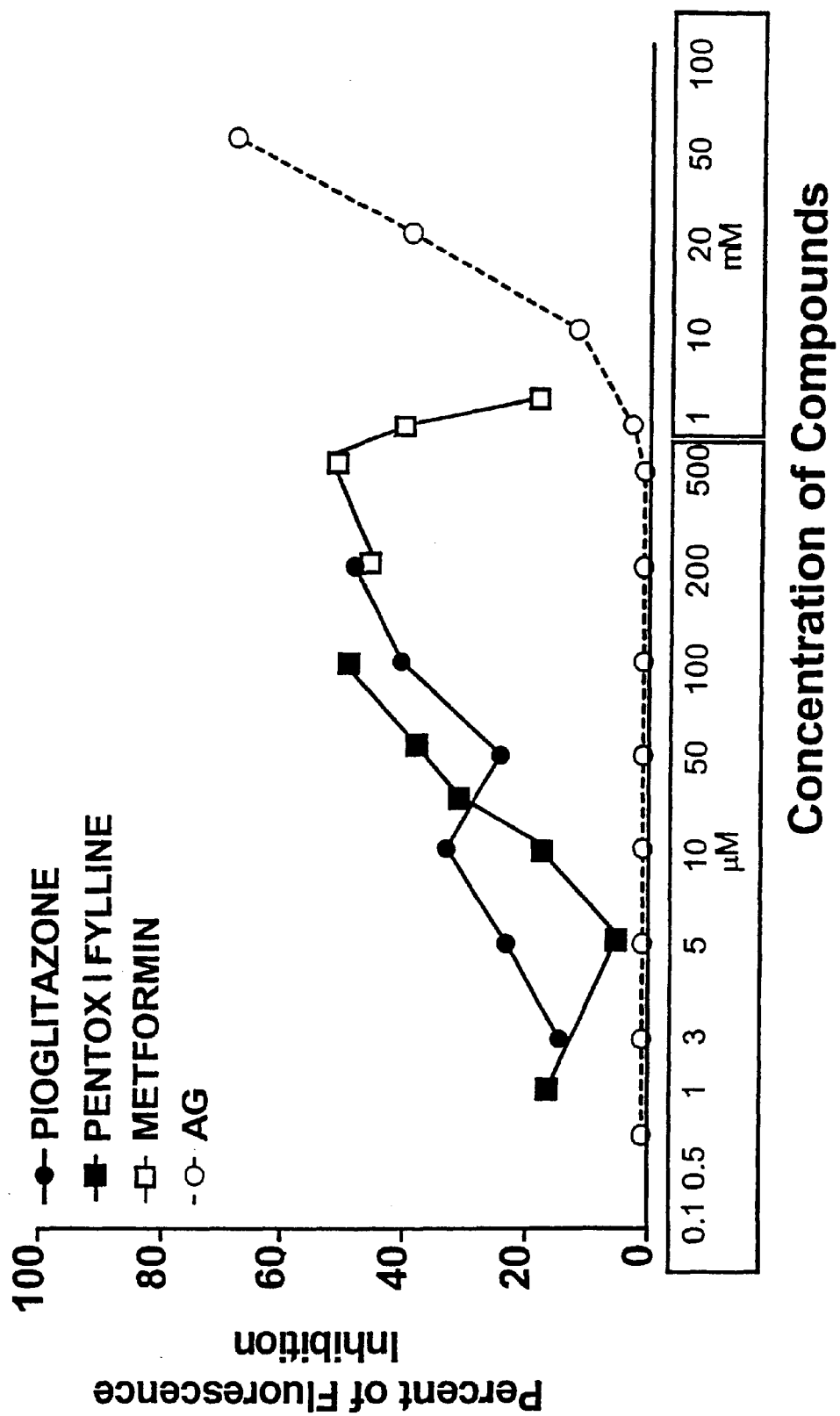
FIG. 2 shows the data from a BSA-glucose assay in the form of dose-response curves for metformin, pioglitazone and pentoxifylline and of AG as a positive control. This assay method is mostly for the inhibitors of late glycation and AGE formation. The results obtained by this assay show all 4 compounds investigated here have strong inhibitory effects on the post-Amadori glycation, AGE formation and AGE-crosslinking.

FIG. 2 shows for each of the three compounds as well as for aminoguanidine the inhibitory effects of for a range of concentrations for each compound. The results obtained by this assay show that all of the compounds have a strong inhibitory effect on the post-Amadori glycation, AGE formation and AGE-crosslinking.

EXAMPLE 3
N-Acetyl-Glycyl-Lysine Methyl Ester (G.K. Peptide)-Ribose Assay Evaluation of the late glycation products (AGE's), and AGE-inhibition by the new inhibitor compounds was tested by incubation of G.K. peptide in ribose in the presence or the absence of the agent, followed by determination of chromophores generated in the course of glycation and AGE formation through determination of their specific fluorescence. The Nagaraj et al. (1996) method used to evaluate the ability of the compounds of the present invention to inhibit the crosslinking of N-acetylglycyl-lysine methyl ester in the presence of ribose was as follows:

Stock Solutions 0.5 M sodium phosphate buffer pH 7.4 containing $NaN_3$ 0.2 g/L

GK peptide (Sigma) 80 mg/mL in 0.5 M sodium phosphate buffer pH 7.4

Ribose 800 mM (120 mg/mL) in 0.5 M phosphate buffer

Equal volumes (0.1 mL) of the 3 stock solutions were mixed together, filtered through a 0.2 micron filter (Corning) and incubated under aseptic conditions for 24 hours at 37° C. The inhibitor compounds were added to a final concentration of 1 millimole/L. At the end of the incubation period, samples were analyzed for their specific fluorescence (excitation, 340 nm; emission, 420 nm). The % inhibition by different concentrations of inhibitor was calculated as described above. Aminoguanidine was used as a positive control.

Figure 3:
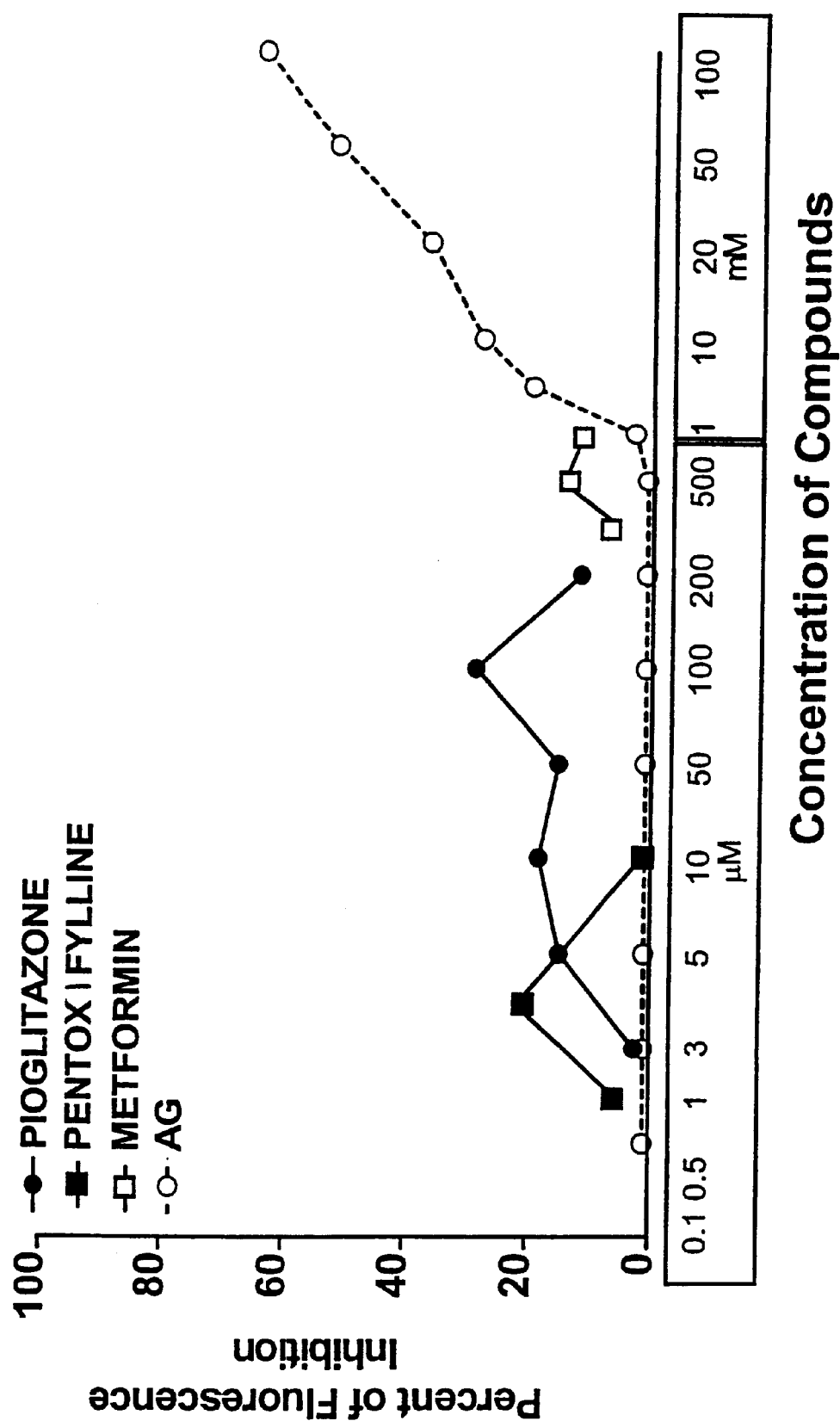
FIG. 3 presents the dose-response curves of the 4 compounds in the study based on the GK-Ribose assay.

FIG. 3 shows the inhibitory effects of each of the compounds to block specific fluorescence of protein-AGE in these separate determinations using the G.K. peptide-ribose assay. The results obtained from this Example and from the results in Example 2 suggest that this type of drug therapy has benefits in reducing the pathology associated with the formation of late glycation products and protein crosslinking.

EXAMPLE 4

ELISA Assay

We have used a special ELISA technique to evaluate the ability of the compounds under this study to inhibit the cross-linking of glycated-BSA (AGE-BSA) to a rat tail-tendon-collagen coated 96 well plate. Cross-linking of AGE-BSA to a rat tail-tendon-collagen coated plate was performed with and without the testing compound at the desired concentrations. The uncross-linked AGE-BSA was then removed by washing the wells. The AGE-BSA cross-linked to the tail-tendon-collagen coated plate was then quantified by a polyclonal antibody raised against AGE-RNAse. Positive results in this assay indicate that the inhibitor is capable of reducing the amount of AGE-BSA which cross-links with collagen. Aminoguanidine was used as positive control.

The following method was used to evaluate the ability of the compounds of the present invention to inhibit the cross-linking of glycated bovine serum albumin (AGE-BSA) to the rat tail-tendon-collagen coated 96-well plate.

The AGE-BSA was prepared by incubating BSA at a concentration of 100 mg per mL with 200 mM glucose in 0.5 M sodium phosphate buffer, pH 7.4 at 37° C. for 12 weeks. The glycated BSA was then extensively dialyzed against phosphate buffer solution (PBS) for 48 hours with an additional 5 buffer exchanges. The rat tail-tendon-collagen coated plate (Biocoat Cell Environment, Becton Dickinson) was blocked first with 200 μL of Superblock blocking buffer (Pierce #37515X) for one hour. The block solution was removed from the wells by washing the plate three times manually with PBS-Tween 20 solution (0.05% Tween 20). Cross-linking of AGE-BSA (0.01 to 1 μg per well depending on the batch of AGE-BSA) to a rat tail-tendon-collagen coated plate was performed with and without the testing compound dissolved in PBS buffer at pH 7.4 at the desired concentrations by the addition of 50 μL each of the AGE-BSA diluted in PBS or in the testing compound at 37° C. for 4 hours. The unbrowned BSA in PBS buffer with or without testing compound was added to the separate wells as the blanks. The uncross-linked AGE-BSA was then removed by washing the wells three times with PBS-Tween buffer. The AGE-BSA cross-linked the tail-tendon coated plate was then quantified by the polyclonal antibody raised against AGE-RNAse. After a one-hour incubation period, AGE antibody was removed by washing 4 times with PBS-Tween.

The bound AGE antibody was then detected by the addition of horseradish peroxidase-conjugated secondary antibody-goat anti-rabbit immunoglobulin and incubation for 30 minutes. The substrate of 2,2'-azino-bis-(3-ethylbenzothiazoline-6-sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows:

$$\% \text{ inhibition} = \frac{\text{optical density (without compound)} - \text{optical density (with compound)}}{\text{optical density (without compound)}} \times 100$$

Figure 4A:
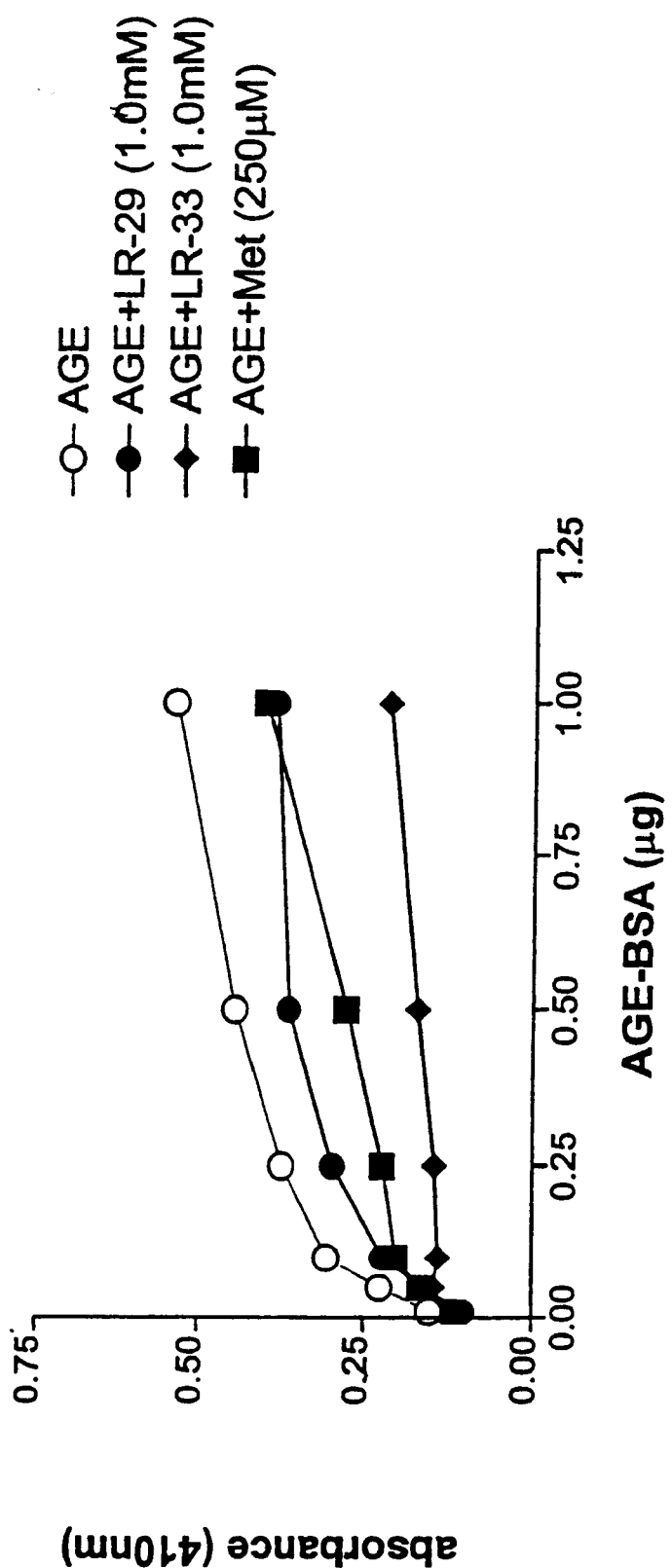
FIG. 4A represents the data from the immunochemical (ELISA) assay that evaluates the ability of an inhibitory compound to inhibit the cross-linking of glycated-BSA (AGE-BSA) preparation to the rat tail-collagen coated 96 well plate. Positive results in this assay indicate the inhibitor is capable of reducing the amount of AGE-BSA that cross-links with collagen. AGE represents AGE-BSA with no inhibitor added. LR-29 (4-(4-chloro-3-nitrobenzoylcarboxamido)phenoxyisobutyric acid) and LR-33 (4-(2-chloro-4-nitrophenylureido)phenoxyisobutyric acid) are two strong inhibitors of AGE-crosslinking developed in our laboratory used at 1 millimolar concentrations. Metformin (Met) was used at 250 micromoles/L. Percent inhibitors were calculated to be 44% for metformin at 250 micromoles/L and 66% for LR-33 at 1 millimole/L concentration.
Figure 4B:
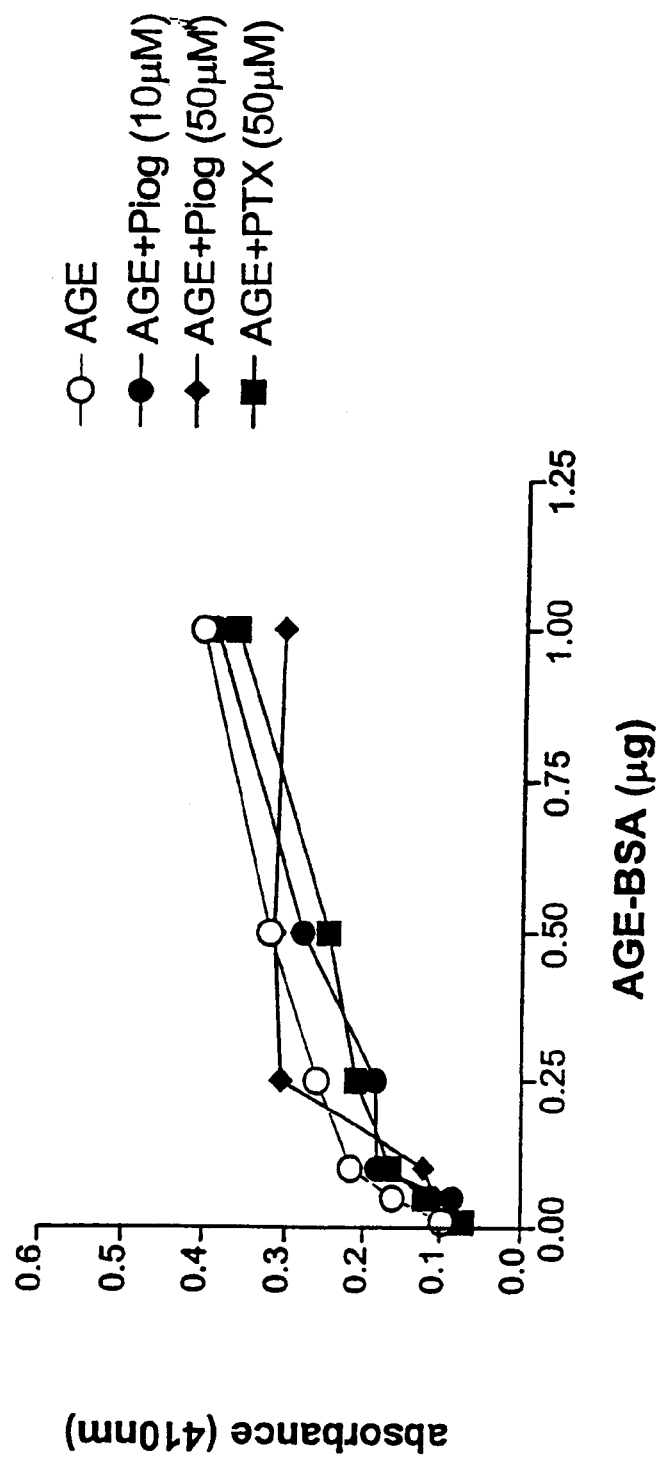
FIG. 4B demonstrates the data from an ELISA assay as described in FIG. 4A. Pioglitazone (Piog) at 10 and 50 micromoles/L and pentoxifylline (PTX) at 50 μM showed inhibitory effects on cross-linking of AGE-BSA to the rat tail-collagen.

The results of testing the compounds with the ELISA method are shown in FIGS. 4A and 4B. FIG. 4A shows the results for metformin at a concentration of 250 μM. The results shown 44% inhibition by metformin and 66% inhibition for LR-33 (4-(2-chloro-4-nitrophenylureido) phenoxyisobutyric acid). FIG. 4B shows the results using pioglitazone at 10 and 50 μM and for pentoxifylline at 50 μM.

The above Examples suggest that this type of drug therapy will be beneficial in reducing the pathology associated with the formation of nonenzymatic glycation products (early and late products) and protein-protein crosslinking. Compounds of the present invention are found to be more potent inhibitors of AGE-formation in vitro as compared to aminoguanidine, which is in phase ⅔ clinical trial to prevent diabetic complications. Previous studies have shown these compounds to be non-toxic. They may be administered orally at variable dosages depending on the activity of each agent in a single or individual amount. In addition, the compounds may be administered parenterally or rectally.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

Airaksinen K E J, et al. (1993). *Cardiovas. Res.* 27:942–945.

Al-Abed Y, et al. (1996). *J. Biol. Chem.* 271:2892–2896.

Baily A J, et al. (1998). *Mechanisms of Aging and Development* 106:1–56.

Baynes J W (1996). "Reactive oxygen in the aetiology and complications of diabetes". In *Drugs, Diet and Disease,*

Vol. 2: Mechanistic Approaches to Diabetes. Ioannides C (ed.) (London, Pergamon), pp. 203–240.
Baynes J W and Thorpe S R (1999). *Diabetes* 48:1–9.
Beisswenger P, et al. (1998). Am. Diab. Assoc., 58th Annual Meeting, #312, Chicago, June 1998.
Beisswenger P J, et al. (1999). *Diabetes* 48:198–202.
Boel E, et al. (1995). *J. Diab. Compl.* 9:104–129.
Booth A A, et al. (1997). *J. Biol. Chem.* 272:5430–5437.
Brownlee M, et al. (1985). *Diabetes* 34:938–941.
Brownlee M, et al. (1986). *Science* 232:1629–1632.
Brownlee M, et al. (1991). *N. Engl. J. Med.* 318:1315–1321.
Bucala R and Cerami A (1992). *Adv. Pharmacol.* 23:1–33.
Bucala R and Vlassara H (1997). *Experimental Physiology* 82:327–337.
Bucala R, et al. (1984). *Proc. Natl. Acad. Sci. USA* 81:105–109.
Bucala R, et al. (1993). *Proc. Natl. Acad. Sci. USA* 90:6434–6438.
Bucala R, et al. (1994). *Proc. Natl. Acad. Sci. USA* 91:9441–9445.
Cameron N E, et al. (1992). *Diabetologia* 35:946–950.
Chen H J C and Cerami A (1993). *J. Carbohydr. Chem.* 12:731–742.
Corbett J A, et al. (1992). *Diabetes* 41:552–556.
Dawnay A and Millar D J (1998). *Cell. Mol. Biol. (Noisy-le-grand)* 44:1081–1094.
Durany N, et al. (1999). *Eur. Arch. Psychiatry Clin. Neurosci.* 249 Suppl. 3:68–73.
Haitoglou C S, et al. (1992). *J. Biol. Chem.* 267:12404–12407.
Hammes H, et al. (1991). *Proc. Natl. Acad. Sci. USA* 88:11555–11563.
Horie K, et al. (1997). *J. Clin. Invest.* 100:2995–3004.
Ikeda K, et al. (1996). *Biochemistry* 35:8075–8083.
Itakura M, et al. (1991). *Life Science* 49:889–897.
Kato S, et al. (1999). *Acta Neuropathol. (Berl.)* 97:260–266.
Kennedy L and Lyons T J (1997). *Metabolism* 46:14–21.
Kikuchi S, et al. (1999). *J. Neurosci. Res.* 57:280–289.
Kochakian M, et al. (1996). *Diabetes* 45:1694–1700.
Koschinsky T, et al. (1997). *Proc. Natl. Acad. Sci. USA* 94:6474–6479.
Li Y M, et al. (1996). *Proc. Natl. Acad. Sci. U.S.A.* 93:3902–3907.
Lindsay M R, et al. (1997). *Clin. Chem. Acta* 263:239–247.
Lucey M D, et al. (2000). *J. Rheumatol.* 27:319–323.
Maillard L C (1916). *Ann. Chem.* 5:258.
Makita Z, et al. (1991). *N. Eng. J. Med.* 325:836–842.
Makita Z, et al. (1992). *Science* 258:651–653.
Makita Z, et al. (1994). *Lancet* 343:1519–1522.
Matsumoto K, et al. (1997). *Biochem. Biophys. Res. Commun.* 24:352–354.
McLellan A C, et al. (1994). *Clin. Sci.* 87:21–29.
McPherson J D, et al. (1988). Biochemistry 27:1901–1907.
Miyata T, et al. (1993). *J. Clin. Invest.* 92:1243–1252.
Monnier V, et al. (1986). *N. Engl. J. Med.* 314:403–408.
Munch G, et al. (1997). *Brain Res. Brain Res. Rev.* 23:134–143.
Munch G, et al. (1998). *J. Neural. Transm.* 105:439–461.
Nagaraj R H, et al. (1996). *J. Biol. Chem.* 271:19338–19345.
Nakamura S, et al. (1997). *Diabetes* 46:895–899.
Newkirk M M, et al. (1998). *Cell. Mol. Biol. (Noisy-le-grand)* 44:1129–1138.
Nicholl I D and Bucala R (1998). *Cell. Mol. Biol. (Noisy-le-grand)* 44:1025–1033.
Nicholls K and Mandel T (1989). *Lab. Invest.* 60:486–491.
Odani H, et al. (1999). *J. Chromatogr. B Biomed. Sci. Appl.* 731:131–140.
Onorato J M, et al. (1998). *Ann. N. Y. Acad. Sci.* 854:277–290.
Panagiotopoulos S, et al. (1998). *Atherosclerosis* 136:125–131.
Phillips S A and Thornalley P J (1993). *Eur. J. Biochem.* 212:101–105.
Rahbar S (1968). *Clin. Chem. Acta* 22:296–298.
Rahbar S, et al. (1969). *Biochem. Biophys. Res. Commun.* 36:838–843.
Rahbar S and Nadler J (1999). *Diabetes* 48 (Suppl. 1):Abstract #1648.
Requena J R, et al. (1997). *J. Biol. Chem.* 272:17473–14479.
Sano H, et al. (1999). *Mech. Ageing Dev.* 107:333–346.
Schalkwijk C G, et al. (1998). *Biochim. Biophys. Acta* 1394:187–198.
Sensi M, et al. (1993). *Diabetologia* 36:797–801.
Shibata N, et al. (1999). *Acta Neuropathol. (Berl.)* 97:240–246.
Silbiger S, et al., (1993). *Kidney Int.* 43:853–864.
Soulis T, et al. (1997). *Diabetologia* 40:1141–1151.
Soulis-Liparota T, et al. (1991). *Diabetes* 40:1328–1334.
Takagi Y, et al. (1995). *J. Diabetes Compl.* 9:87–91.
Takayama F, et al. (1998). *Cell. Mol. BioL (Noisy-le-grand)* 44:1101–1109.
The Diabetes Control and Complications Trial Research Group (1993). *N. Engl. J. Med.* 329:977–986.
Tilton R G, et al. (1993). *Diabetes* 42:221–232.
Ulrich P and Zhang X (1997). *Diabetologia* 40:5157–5159.
Vasan S, et al. (1996). *Nature* 382:275–278.
Vlassara H, et al. (1994). *Lab. Invest.* 70:138–151.
Vlassara H, et al. (1995). *Mol. Med.* 1:447–456.
Westwood M E, et al. (1997). *Biochim. Biophys. Acta* 1356:84–94.
Yim H S, et al. (1995). *J. Biol. Chem.* 270:28228–28233.

What is claimed is:

1. A method of inhibiting formation of glycation endproducts in an organism, wherein said method comprises administering an effective amount of a compound or a pharmaceutically acceptable salt of said compound to said organism wherein said compound is selected from the group consisting of pentoxifylline, pioglitazone.

2. A method of inhibiting protein-protein cross-linking in an organism, wherein said method comprises administering an effective amount of a compound or a pharmaceutically acceptable salt of said compound to said organism wherein said compound is selected from the group consisting of pentoxifylline and pioglitazone.

* * * * *

UNITED STATES PATENT AND TRADEMARK OFFICE
CERTIFICATE OF CORRECTION

PATENT NO. : 6,693,106 B2
DATED : February 17, 2004
INVENTOR(S) : Samuel Rahbar and Jerry L. Nadler It is certified that error appears in the above-identified patent and that said Letters Patent is hereby corrected as shown below:

Column 1,
Line 47, replace "contripbute" with -- contribute --.

Signed and Sealed this

Tenth Day of January, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,693,106 B2 | Page 1 of 1 |
| APPLICATION NO. | : 10/096579 | |
| DATED | : February 17, 2004 | |
| INVENTOR(S) | : Samuel Rahbar and Jerry L. Nadler | |

It is certified that error appears in the above-identified patent and that said Letters Patent is hereby corrected as shown below:

At Column 1, line 47, replace "contripbute" with --contribute--.

Signed and Sealed this

Twenty-ninth Day of August, 2006

JON W. DUDAS
*Director of the United States Patent and Trademark Office*